United States Patent [19]

Lancaster et al.

[11] Patent Number: 4,917,682

[45] Date of Patent: Apr. 17, 1990

[54] LEAK RESISTANT ELASTIC WAIST DIAPER

[75] Inventors: Eugene P. Lancaster, Gig Harbor; Andrew Urban, III, Sumner, both of Wash.

[73] Assignee: Weyerhaeuser Company, Tacoma, Wash.

[21] Appl. No.: 118,831

[22] Filed: Nov. 9, 1987

Related U.S. Application Data

[63] Continuation-in-part of Ser. No. 850,183, Apr. 10, 1986, 4,726,807.

[51] Int. Cl.⁴ ............................................. A61F 13/16
[52] U.S. Cl. .................................................... 604/385.2
[58] Field of Search .................. 604/385.1, 385.2, 358, 604/366, 370

[56] References Cited

U.S. PATENT DOCUMENTS

| | | |
|---|---|---|
| Re. 26,151 | 1/1967 | Duncan et al. |
| 1,544,312 | 6/1925 | Gray |
| 2,200,429 | 5/1940 | Perrin et al. |
| 2,905,581 | 9/1959 | Maxey |
| 2,953,551 | 9/1960 | White ............................... 260/86.7 |
| 3,086,242 | 4/1963 | Cook et al. ............................ 18/1 |
| 3,245,407 | 4/1966 | Mason |
| 3,265,765 | 8/1966 | Holden ............................... 260/876 |
| 3,520,303 | 7/1970 | Endres ................................. 128/287 |
| 3,551,540 | 12/1970 | Pellicciari et al. ..................... 264/89 |
| 3,629,039 | 12/1971 | Frick .................................... 156/269 |
| 3,639,917 | 2/1972 | Althouse ............................... 2/270 |
| 3,755,062 | 8/1973 | Schirmer ............................. 161/146 |
| 3,819,401 | 2/1974 | Massengale et al. ................. 156/85 |
| 3,844,288 | 10/1974 | Kiela |
| 3,860,003 | 1/1975 | Buell |
| 3,912,565 | 10/1975 | Koch et al. ........................... 156/85 |
| 3,951,150 | 4/1976 | Schaar |
| 4,050,462 | 9/1977 | Woon et al. |
| 4,205,679 | 6/1980 | Repke et al. |
| 4,253,461 | 3/1981 | Strickland et al. |
| 4,324,245 | 4/1982 | Mesek et al. |
| 4,333,782 | 6/1982 | Pieniak ............................... 156/164 |
| 4,337,771 | 7/1982 | Pieniak et al. |
| 4,352,355 | 10/1982 | Mesek et al. |
| 4,381,781 | 5/1983 | Sciaraffa et al. ..................... 604/372 |
| 4,405,397 | 9/1983 | Teed .................................... 156/164 |
| 4,413,623 | 11/1983 | Pieniak ............................... 604/365 |
| 4,430,086 | 2/1984 | Repke ................................. 604/385 |
| 4,437,860 | 3/1984 | Sigl et al. ............................ 604/385 |
| 4,486,192 | 12/1984 | Sigl .................................... 604/385 |
| 4,515,595 | 5/1985 | Kievit et al. ......................... 604/385 |
| 4,563,185 | 1/1986 | Reiter ................................. 604/385 |
| 4,582,550 | 4/1986 | Sigl .................................... 604/385.2 |
| 4,726,807 | 2/1988 | Young et al. ........................ 604/385.2 |

FOREIGN PATENT DOCUMENTS

| | | |
|---|---|---|
| 866819 | 5/1961 | United Kingdom |
| 866820 | 5/1961 | United Kingdom |
| 866821 | 5/1961 | United Kingdom |
| 866822 | 5/1961 | United Kingdom |
| 1010064 | 11/1965 | United Kingdom |
| 2136677A | 3/1983 | United Kingdom |
| 2136678A | 3/1983 | United Kingdom |

*Primary Examiner*—John D. Yasko

[57] ABSTRACT

The present invention is a disposable diaper having an insert piece located transversely across at least one of the waist contacting ends of the diaper between the backing and the cover sheets. This piece overlies the filler pad between the pad and skin contacting cover sheet and serves to prevent liquid leakage from the pad in the waist zones. The insert pieces are made from a heat shrinkable elastomeric material of the type that is heat unstable and relatively inelastic in its unshrunk form and stable and relatively elastic in its heat shrunk. The ends of the insert pieces adjacent the waist margins are heat shrunk to provide an elasticized waist on the diaper which further serves to prevent leakage in this area.

5 Claims, 1 Drawing Sheet

U.S. Patent    Apr. 17, 1990    4,917,682
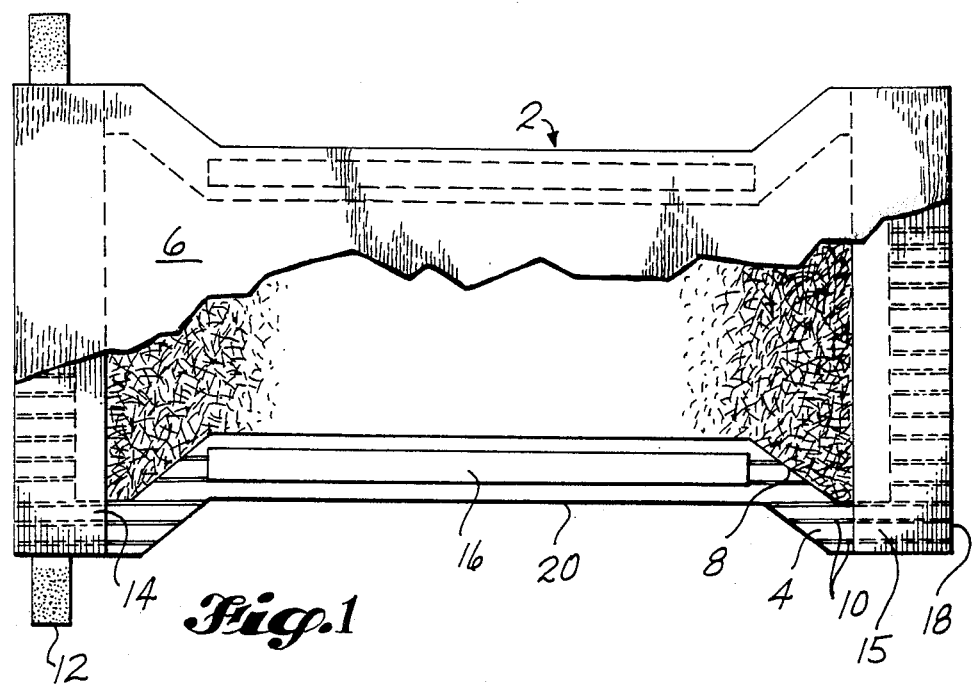
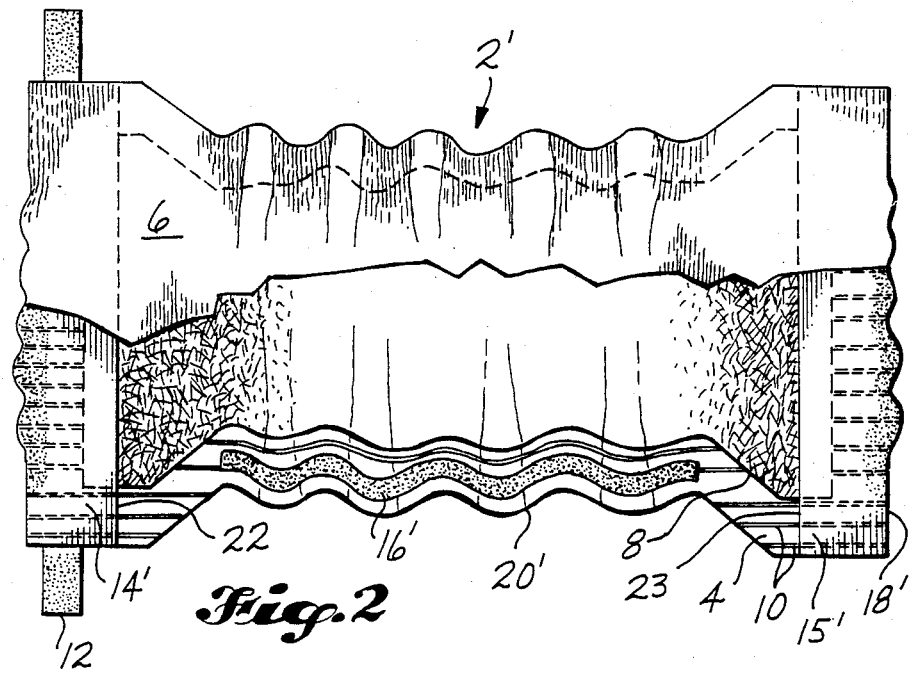

LEAK RESISTANT ELASTIC WAIST DIAPER

This application is a continuation-in-part of Ser. No. 850,183, filed April 10, 1986, now U.S. Pat. No. 4,726,807.

BACKGROUND OF THE INVENTION

The present invention comprises a disposable diaper having elasticized leg and/or waist encircling areas, and a method and apparatus for manufacture of the diapers. The elastic areas are provided by a heat shrinkable elastomeric material of the type that is heat unstable and relatively inelastic in its unshrunk form and stable and relatively elastic in its heat shrunk form.

Garments having localized elasticized areas for ensuring relatively tight fits around such body zones as wrists, waist or thighs have long been manufactured. Initially, and still to a certain extent, the elastic has been applied by sewing while held in a stretched condition. When relaxes, the elastic causes a shirring or puckering of the elasticized area of the garment. Sewing elastic is a relatively slow and expensive manufacturing operation. Many inventors have dedicated their energy to finding simpler methods of attaching elastic. As one example, Gray, U.S. Pat. No. 1,544,312, used a partially cured rubber strip which was mechanically crimped to the garment and later heat cured. Maxey, U.S. Pat. No. 2,905,181, used a band of nitrile rubber which was heat sealed to a moisture impervious polyvinyl chloride film.

Disposable diapers for infants have been the subject of a great deal of inventive activity to prevent leakage. One very successful effort in this regard was the use of a box pleat around the thigh areas of an infant. A diaper of this type is described by Duncan et al in U.S. patent Reissue 26,152. While this construction represented a major step forward, it still did not provide an entirely satisfactory solution to the problem of leakage. Another move toward an ultimate solution is described by Buell in U.S. Pat. No. 3,860,003. The Buell diaper used narrow ribbons of stretched elastic along each longitudinal side margin in the thigh encircling areas. This construction has been so highly successful that it has been emulated and improved upon by subsequent inventors in the field. The following U.S. Patents are exemplary of these later developments: Woon et al, U.S. Pat. No. 4,050,462; Strickland et al, U.S. Pat. No. 4,253,461; Sigl et al, U.S. Pat. No. 4,437,860; and Teed, US. Pat. No. 4,405,397. The Strickland et al product represents a move beyond diapers suitable only for infants and is a product principally adapted for use by incontinent adults. Schaar, in U.S. Pat. No. 3,951,150, shows an infant diaper having an elasticized waist encircling area designed for reducing leakage from that portion of the product.

The above list is presented primarily to indicate historical development of diapers having elasticized zones and is not intended to be fully inclusive of all such products which have been developed. All of these examples use an elastic material which is normally a relatively narrow ribbon of natural rubber adhesively bonded between the backsheet and cover sheet of the diaper. The use of adhesive bonding, usually with flexible hot melt adhesives, has enabled the production of elasticized disposable diapers at high rates of speed.

During the later part of the time period represented by the above patents, a parallel approach has been developing using non-rubber elastomeric materials. These are based on a wide variety of synthetic polymers which typically are uniaxially or biaxially stretched during their manufacture into relatively thin film. This stretching induces stresses which are frozen into the product when it is cooled while being held under uniaxially or biaxially applied tension. Certain of these materials retain a memory of their dimensions in the original unstretched state. Depending on the particular polymer chosen, and its method of manufacture, by heating to a specific predetermined temperature, the material will shrink back to approximately this original dimension. These polymeric products can be readily tailored to be of elastomeric nature. The term "elastomeric" is interpreted in various ways, but here it is generally meant to mean that a product may be stretched to at least about 120–140% of its original length and return to that length without permanent deformation when the stretching force is released. Many of the products available are relatively inelastic in their uni- or biaxially oriented heat unstable forms and would not meet the above criterion. however, these become fully elastic when heat shrunk. A further feature of many of these polymers is that they can be heat sealed or bonded to other materials at a temperature below the point which will cause heat shrinkage. This is especially convenient for the manufacture of elasticized garments since it infers that the material may be applied without the need to be held under tension. A subsequent heating step is all that is needed to produce an elasticized zone.

While many polymeric materials of generically different types can be cited as being useful in the above application, the following U.S. patents should be considered as being exemplary: Perrin et al, U.S. Pat. No. 2,200,249; White, U.S. Pat. No. 2,953,551; Cook et al, U.S. Pat. No. 3,086,242; Holden et al, U.S. Pat. No. 3,265,765; and Pellicciari et al, U.S. Pat. No. 3,551,540. The following British patents also disclose useful polymer compositions: 866,819; 866,820; 866,821; 866,822; and 1,010,064.

The original application of heat shrunk elastic to garments appears to have been done by mason as shown in U.S. Pat. No. 3,245,407. Here the inventor produced plastic panties with heat shrunk elasticized leg and waist zones. Mason showed other applications as well. Later, Althouse in U.S. Pat. No. 3,639,917 showed the use of heat shrinkable elastic ribbons in other applications such as wrist cuffs on disposable hospital garments. Massengale et al, in U.S. Pat. No. 3,819,401, and Koch et al, in U.S. Pat. No. 3,912,565 show the use of specific heat shrinkable materials for making elasticized areas in garments such as panties. Schirmer, in U.S. Pat. No. 3,755,062, shows the use of a film of heat shrinkable materials for making bulked fabric articles such as nonwoven rugs.

Natural rubber is a relatively expensive product and for this and other reasons, it is normally used in the form of threads or relatively narrow ribbons when used to elasticize portions of garments. A disadvantage of this construction is that the elasticized portion of the garment frequently presents a small and very narrow bearing area against the skin of the wearer. Thus, if the purpose of the elasticized area is to prevent leakage, as in the case of an elastic leg diaper, the elastic must be held under relative high tension to provide a tight seal. This will frequently result in chafing and general discomfort to the wearer. One solution to this problem has been to use parallel narrow strips of rubber elastic to increase the bearing area. A diaper having this type of construction is seen in Repke, U.S. Pat. No. 4,430,086.

While this approach has been effective, it is relatively expensive because of the additional elastic required. It also considerably complicates manufacture of the product. For this reason, disposable diaper designers have turned to the use of heat shrunk elastomers which can be used in the form of relatively wider ribbons to increase bearing area.

Heat shrinkable materials became of interest to diaper designers as another method for overcoming the cutting and chafing problem caused by narrow elastic. A considerable number of patents have issued, beginning about 1980, directed to the use of heat shrinkable elastic ribbons placed in marginal areas of disposable diapers. In some of these the heat shrinkable elastomer is used only in the leg area, along the longitudinal margins. In others it is used only in the waist area along the transverse margins of the diaper. In still other constructions, the heat shrinkable elastic is used in both locations. Representative examples of disposable diapers using heat shrunk elastic are found among the following U.S. patents: Repke et al, U.S. Pat. No. 4,205,679 and 4,430,086; Mesek et al, U.S. Pat. No. 4,324,245 and 4,352,355; Pieniak, U.S. Pat. No. 4,333,782; Pieniak et al, U.S. Pat. No. 4,337,771 and 4,413,623; Sciaraffa et al, U.S. Pat. No. 4,381,781; Sigl, U.S. Pat. No. 4,486,192; Kievit et al, U.S. Pat. No. 4,515,595; and Relter, U.S. Pat. No. 4,563,185. The following British patent applications are also of interest: Lash, GB 2,136,677A and Chapman et al, GB 2,136,678A.

All of the above patents use discrete ribbons of the heat shrinkable elastic material. These differ greatly in configuration, location, method of attachment, and area in which they are heat shrunk.

Some attention has been given in the past to means for reducing leakage in the waist portions of diapers. Endres, in U.S. Pat. No. 3,520,303 shows a transverse insert portion of polyethylene film overlying each end of the absorbent pad. Kiela, U.S. Pat. No. 3,844,288, shows a similar system. Frick, U.S. Pat. No. 3,629,029, describes machinery for manufacturing diapers having a moisture impermeable insert in the waist area.

SUMMARY OF THE INVENTION

The present invention concerns a diaper having elastic waist, and optionally leg, areas formed using insert strips of heat shrinkable elastomeric materials located in the appropriate marginal zones. These heat shrinkable elastomeric materials are those which are heat unstable and relatively inelastic in their unshrunk form and stable and relatively elastic in their heat shrunk form. They comprise discrete strips located along the appropriate marginal areas of the diapers.

The method by which the diapers are made includes uniting the individual components to form a continuous end-to-end or side-by-side assembly of diaper units, the end-to-end relationship being preferred. The area adjacent adjoining diaper units preferably forms the waist encircling areas of the diapers. These assemblies are maintained under sufficient longitudinal tension to prevent wrinkling during the manufacturing process. At an appropriate point in time transverse inserts of the heat shrinkable elastomeric material are laid over the ends of each absorbent pad in the waist zone. This is normally done when the spaced apart pad units are laid on the backsheet and before the cover sheet is applied. The inserts are normally long enough so that they bridge between two adjacent diaper units, although this is not absolutely essential At some point after the cover sheet has been applied over the assembly, heat is applied to the transverse waist portions to shrink the inserted material and create elasticized areas. The portion of the inserts overlying the absorbent pad is not heated and remains unaffected and dimensionally unchanged. Heating is preferably done in the appropriate localized areas with a hot roll or other means. preferably, simultaneously with the heating or immediately thereafter, individual diapers are severed from the diaper units to release any transverse tension that might be present. This permits the heat treated end portions of the diaper units to shrink freely until they have sufficiently cooled to become heat stable and elastic. Alternatively, the diaper assembly is allowed to remain intact during transverse shrinkage and the transverse tension is relaxed by some other means, such as festooning the assembly between two roll pairs.

Longitudinal inserts of the heat shrinkable elastomeric material may be used in addition to those just described to provide elasticized leg areas as well as elasticized waist zones. Conventional elastic, e.g., natural rubber ribbon or threads, may also be used if desired.

Alternatively, the entire moisture impermeable backsheet may be made from the heat shrinkable elastomeric material. In this case both the backsheet and inserted pieces are heat shrunk in the waist zones to their elastic state.

Where longitudinal inserts of heat shrinkable material are used along the leg areas, or where the entire backsheet is heat shrinkable elastomeric material and it is desired to provide elasticized leg zones, at some point an appropriate area of the longitudinal edges of each diaper unit is heated to a temperature sufficiently high to enable shrinkage of the elastomeric material. Immediately thereafter the marginal longitudinal tension is relaxed while tension is maintained in the central portion of the assembly. The marginal tension is kept in relaxed condition for a sufficient time for the heated elastomeric material to shrink and cool to a temperature where it is again stable, thereby creating marginal elasticized zones on the diapers.

This may be accomplished by running the assembly after marginal heating over a series of rolls which are cylindrical in the central portion but tapered at each end. The heated edges of the diaper overhang the tapered portions. In this manner, as the edges shrink the circumferential distance they travel over the tapered ends of the rolls is significantly less than the circumferential distance traveled by the central portion of the diaper assembly. A sufficient number of rolls are employed to permit the desired marginal shrinkage to occur and to further allow the heated areas to cool to the point that they are again stable. At some point beyond this, when the heat treated and now elastic marginal portions have again become stable, they can once more be stretched, if desired, as the assembly moves further through the diaper making machinery.

It is an object of the present invention to provide a leak resistant disposable diaper having at least one elastic waist portion.

It is another object of the invention to provide a diaper in which a transverse insert overlying the absorbent pad gives leak resistance and further serves to elasticize the waist zone.

these and many other objects will become readily apparent to those skilled in the art upon reading the following detailed description taken in conjunction with the drawings.

BRIEF DESCRIPTION OF THE DRAWINGS

FIG. 1 is a plan view, partically cut away, showing a diaper of the present invention in an as assembled configuration before the waist portions are elasticized.

FIG. 2 is similar to FIG. 1 but shows the finished diaper with elasticized waist portions.

DESCRIPTION OF THE PREFERRED EMBODIMENTS

In the description that follows, it will be understood by those skilled in the art that certain terms are relative. Most disposable diapers and adult incontinent pads are assembled in a continuous end-to-end fashion. In this case the sides of the diaper, which wrap around the upper thighs of the wearer, is the longitudinal direction. However, it is known for diapers to be manufactured in a continuous side-to-side assembly as, for example, is shown in Joa, U.S. Pat. No. 4,284,454. In this case, the ends, or waist encircling portion of the diaper is in the longitudinal direction of motion during manufacture. Thus, the terms "longitudinal" and "transverse" are relative and as used herein should not be considered as limiting to one orientation or the other.

The various embodiments of the present invention can most readily be understood by reference to the attached drawings. FIG. 1 shows a diaper 2 whose components have been fully assembled but which is as yet in an unfinished state of manufacture. This is the form of a diaper unit as they are most commonly found while under light tension in an end-to-end assembly on a diaper making machine. It comprises a moisture impervious backsheet 4 which would normally be made from a lightly textured pigmented polyethylene. Backing sheet 4 is overlaid by a moisture absorbent fluff filler pad 8. This, in turn, is overlaid at its ends by an insert strip of moisture impervious material 14, 15. In the present case this insert strip is a biaxially oriented heat shrinkable thermoplastic material. The insert is shown here in its relatively inelastic heat unstable, unshrunk state. When heat shrunk it becomes elastic having an extensibility of up to 100%, or even greater. The assembly is then covered before any heat treatment by a moisture pervious nonwoven top sheet 6. The entire assembly is bonded together by a plurality of fine hot melt adhesive lines 10. Adhesive tabs 12 are conventional and are used by the mother for attachment of the diaper to the infant.

Optionally, inserted strips 16 of the heat shrinkable latent elastic material may be inserted along longitudinal margins 20 to ultimately elasticize the leg areas. It is within the scope of the invention to use conventional rubber elastic at this location. The units are severed from a continuous assembly to form end or waist margins 18.

FIG. 2 shows the diaper of FIG. 1 in which the waist and longitudinal margins have been heat shrunk to form elastic portions. These ensure a tight fit and are important in preventing leakage when worn by an infant or adult user. The diaper of FIG. 2 is shown without any longitudinal or transverse restraint. As a result, the heat shrunk marginal areas 18', 20' will tend to form a shirred or wrinkled edge with accompanying folds. When placed on a wearer the shirred edges are generally placed under tension and the diaper surface is again drawn reasonably flat. In FIG. 2 the prime (') symbol indicates portions of the diaper of FIG. 1 which are subsequently modified by heat shrinking the inserted pieces.

The temperature to which the longitudinal edge of a diaper of the type shown in FIGS. 1 and 2 must be heated is dependent upon the particular polymeric material which is used. These temperatures will generally range between about 80° to 120° C. The amount of shrinkage obtained is dependent upon the temperature to which the polymeric material is heated, that time it is held at that temperature, and the degree to which it is allowed to relax while being cooled.

In the present case the transversely inserted pieces 14', 15', as shown in FIG. 2, have only the outer marginal edge 18' heat shrunk and elasticized. Inner edges 22, 23 are left unchanged. here they serve to prevent moisture leakage in the waist areas of the diaper.

EXAMPLE 1

The various components used in the manufacture of infant diapers or adult incontinent pads are well known within the industry. The moisture permeable top or body contacting sheet has a basis weight usually in the range of 18–26 g/m$^2$ and may typically be a carded polyester fiber with a latex binder or spun bonded polypropylene having continuous fibers of 2–5 denier thermally bonded by patterned calendar rolls. Respective examples of these types would be Scott 6822, available from Scott Paper Company, Nonwovens Division, Philadelphia, Pennsylvania or Celestra, available from James River Corporation, Washougal, Washington. The moisture impermeable diaper backing sheet may be a low density polyethylene film having a thickness in the range of 0.02–0.04 mm (0.75–1.5 mils). This material is frequently microembossed to better retain attachment tapes. An example of such a conventional backing material would be Clopay Code 53, available from Clopay Corporation, Cincinnati, Ohio.

An alternative type of backing film is a biaxially oriented heat shrinkable elastomeric material of the type that is heat unstable and relatively inelastic in its unshrunk form and stable and relatively elastic in its heat shrunk form. This may be used either for the entire backing sheet or for ribbon-like inserts along the marginal portions of the backing sheet. One such material is Cryovac SDX-0820, available from Cyrovac Division, W. R. Grace Company, Duncan, South Carolina. This material is a biaxially oriented irradiated polyethylene that becomes heat shrinkable at temperatures generally falling within the range between 80°–95° C. Unrestrained shrinkage after heating this material to the above temperature range will generally be to about 50% of original dimensions. Lower shrinkage can be achieved in one of several ways. Control of the amount of stretch during film formation is one suitable way. As one example, if it is only desired to produce elasticized leg opening areas on a diaper, a uniaxially oriented film would normally be quite suitable. Control of temperature to which the film is heated, and the subsequent rate of cooling, is another way in which shrinkage can be controlled.

Flexible rapid setting hot melt adhesives, which may be used to bind separate heat shrinkable ribbons and may also be used as the fine line adhesives for uniting the entire assembly, are commonly formulated from ethylene-vinyl acetate resins used with tackifiers and other additives. These adhesives tend to be somewhat tacky and flexible at room temperature. One suitable material is available from H. B. Fuller Company, Vadnais Heights, Minnesota as Type HL 1048N.

Large sized infant diapers were made using the above components. These diapers were 495 mm long and 337 mm wide and weighed a total of 72 g. The pad was fluffed bleached kraft softwood pulp having a density in the range of 0.07–0.08 g/cm$^3$. The polyethylene backing film had a thickness of 0.03 mm. An insert of the Cryovac film noted above is placed so as to cover the end portions of two adjacent diapers and overlap the pad portions by about 20–25 mm before the nonwoven top sheet was laid on. This film was coated on the surface facing the nonwoven with parallel fine line adhesive strips so that it was bonded to both the backsheet and topsheet. The longitudinal dimension of the film in each diaper was about 60–70 mm. After this the transverse waist areas were heated to a temperature of approximately 90° C. over a width of about 15 mm and allowed to shrink freely. The ultimate diaper had an extensiblity of about 40% in the waist areas.

EXAMPLE 2

A series of diapers was made as in Example 1 but with the addition of strips of the Cryovac heat shrinkable elastomeric film along each longitudinal margin in the leg area. These strips were about 305 mm long and 10 mm wide. After assembly the longitudinal margins were heated at a temperature of about 95° C. over their entire width using a hot roll and allowed to shrink. Subsequently the transverse waist areas were heated to a slightly lower temperature, as described above. Extensibility in the elasticized leg area approached 80% and was about 40% in the waist areas.

EXAMPLE 3

Another series of diapers was made as in Example 1 but here the polyethylene backing film was replaced with the Cryovac material which had a thickness of 0.03 mm.

The waist and leg areas were heated as in Example 2. The resulting diaper had a leg area extensibiliy of about 30–40% and waist area extensibility of 20–30%.

It will be readily apparent to those skilled in the art that many variations could be made without departing from the spirit of the present invention. Thus, the invention is to be considered as being limited only by the following claims.

We claim:

1. In a disposable diaper of the type having a coextensive moisture permeable skin contacting cover sheet and a moisture impermeable backing sheet with a moisture absorbing filler pad disposed therebetween, said pad being of smaller longitudinal and transverse dimensions than said cover and backing sheets to form pad free zones around the margins of the diaper, said diaper having longitudinal leg contacting edges and transverse waist contacting ends, the improvement which comprises:
   an insert piece located transversely across at least one of the waist contacting ends of the diaper between the backing and cover sheets,
   said insert piece overlapping the filler pad between said pad and the skin contacting cover sheet and serving to prevent liquid leakage from the pad to the waist contacting end,
   said insert piece being made from a heat shrinkable elastomeric material of the type that is heat unstable and relatively inelastic in its unshrunk form and stable and relatively elastic in its heat shrunk form,
   said insert piece being bonded to at least one of the cover or backing sheets in the waist zone and heat shrunk to its relatively elasticized state in said zone to provide a leak resistant diaper with at least one elasticized waist portion.

2. The disposable diaper of claim 1 which has insert pieces located at both ends of the diaper and each insert piece is heat shrunk to provide an elasticized waist portion at each end.

3. The disposable diaper of claim 1 which further has insert pieces along each leg contacting edge, said leg inserts lying outside the absorbent pad and being heat shrunk to provide elasticized edges.

4. The disposable diaper of claim 1 in which the insert piece is bonded to both of the cover and backing sheets in the waist zone.

5. The disposable diaper of claim 1 in which the backing sheet is also made of a heat shrinkable elastomeric material of the type that is heat unstable and relatively inelastic in its unshrunk form and stable and relatively elastic in its heat shrunk form.

* * * * *